(12) United States Patent
Mortensen

(10) Patent No.: US 11,864,886 B2
(45) Date of Patent: Jan. 9, 2024

(54) HEARING DIAGNOSTIC SYSTEM

(71) Applicant: Analog Devices, Inc., Norwood, MA (US)

(72) Inventor: Mikael Mortensen, Milpitas, CA (US)

(73) Assignee: Analog Devices, Inc., Wilmington, MA (US)

( * ) Notice: Subject to any disclaimer, the term of this patent is extended or adjusted under 35 U.S.C. 154(b) by 319 days.

(21) Appl. No.: 16/862,864

(22) Filed: Apr. 30, 2020

(65) Prior Publication Data

US 2020/0345278 A1    Nov. 5, 2020

Related U.S. Application Data

(60) Provisional application No. 62/840,645, filed on Apr. 30, 2019.

(51) Int. Cl.
  *A61B 5/12*     (2006.01)
  *H04R 1/10*     (2006.01)
  *A61B 5/00*     (2006.01)

(52) U.S. Cl.
  CPC ............ *A61B 5/125* (2013.01); *A61B 5/6803* (2013.01); *A61B 5/7217* (2013.01);
  (Continued)

(58) Field of Classification Search
  CPC .... H04R 25/70; H04R 1/1008; H04R 1/1083; H04R 1/1091; H04R 29/001; H04R 5/033; H04R 1/1016; H04R 1/1041; H04R 2430/03; H04R 2460/15; H04R 25/40; H04R 3/04; H04R 2460/03; H04R 1/10; H04R 5/04; H04R 2205/041; H04R 2420/01; H04R 2420/07; H04R 25/554; H04R 25/75; H04R 3/005; H04R 7/04; H04R 7/16; H04R 9/02; H04R 9/025; H04R 9/04; H04R 9/047; H04R 25/505; H04R 1/1066; H04R 1/2811; H04R 2225/55; H04R 2460/01; H04R 25/305;
  (Continued)

(56) References Cited

U.S. PATENT DOCUMENTS 5,999,856 A    12/1999 Kennedy
6,447,461 B1    9/2002 Eldon
(Continued)

FOREIGN PATENT DOCUMENTS

WO    2016071221 A1    5/2016

OTHER PUBLICATIONS

Masalski et al., *Hearing Test on Mobile Devices: Evaluation of the Reference Sound Level by Means of Biological Calibration*, Journal of Medical Internet Research, Mar. 26, 2019, 19 pages.
(Continued)

*Primary Examiner* — Lun-See Lao
(74) *Attorney, Agent, or Firm* — ARENTFOX SCHIFF LLP

(57) ABSTRACT

Herein disclosed is a system that may be implemented within a headphone to facilitate hearing testing. Implementation of the system in the headphone may include implementation of tone generation circuitry and sound pressure level measurement circuitry being implemented in the headphone limiting the amount of calibration for accurate measurement when performing a hearing test.

20 Claims, 11 Drawing Sheets

(52) U.S. Cl.
CPC ......... *H04R 1/1083* (2013.01); *H04R 1/1091* (2013.01); *A61B 2560/0223* (2013.01); *H04R 2460/01* (2013.01)

(58) Field of Classification Search
CPC ........ H04R 1/105; H04R 1/1075; H04R 1/28; H04R 2225/43; H04R 2225/83; H04R 2430/01; H04R 25/50; H04R 25/558; H04R 1/12; H04R 1/20; H04R 1/42; H04R 11/02; H04R 2201/10; H04R 2201/107; H04R 2205/024; H04R 2225/41; H04R 2400/01; H04R 2430/00; H04R 2460/07; H04R 2460/11; H04R 2460/13; H04R 25/353; H04R 25/356; H04R 25/453; H04R 25/502; H04R 25/55; H04R 25/606; H04R 25/652; H04R 25/654; H04R 25/656; H04R 3/00; A61K 31/145; A61K 31/164; A61K 31/185; A61K 31/195; A61K 31/197; A61K 31/27; A61K 31/325; A61K 31/42; A61K 31/428; A61K 31/44; A61K 31/445; A61K 31/55; A61K 31/64; A61K 45/06; A61K 9/0053; A61K 9/2004; A61K 31/65; A61K 31/663; A61K 31/19; A61K 31/506; A61K 33/04; A61K 47/02; A61K 47/10; A61K 47/20; A61K 9/0019; A61K 9/0046; A61K 9/06; G10K 11/17854; G10K 11/17861; G10K 11/17881; G10K 11/16; G10K 11/17885; G10K 2210/1081; G10K 11/17815; G10K 11/17817; G10K 11/17823; G10K 11/17853; G10K 11/17855; G10K 11/1787; G10K 11/17875; G10K 2210/116; G10K 2210/3028; G10K 2210/3055; G10K 2210/504; G10K 11/1785; H04S 7/301; H04S 1/005; H04S 2420/01; H04S 3/00; H04S 3/004; H04S 7/30; G10H 1/0066; G10H 2220/371
USPC ............ 381/60, 312, 92, 94.1–94.5; 600/559
See application file for complete search history.

(56) References Cited

U.S. PATENT DOCUMENTS

| | | | |
|---|---|---|---|
| 7,016,504 B1 | 3/2006 | Shennib | |
| 8,529,464 B2 | 9/2013 | Wasden et al. | |
| 9,326,706 B2 | 5/2016 | Shennib | |
| 10,045,128 B2 | 8/2018 | Shennib | |
| 10,085,678 B2 | 10/2018 | Shennib | |
| 2007/0195965 A1 | 8/2007 | Thomasson et al. | |
| 2009/0304202 A1* | 12/2009 | Somasundaram ... | H04R 29/007 381/82 |
| 2010/0310101 A1* | 12/2010 | Anderson ............ | A61B 5/6803 381/314 |
| 2011/0137111 A1* | 6/2011 | Hanley ................. | H04R 25/75 600/28 |
| 2011/0176685 A1* | 7/2011 | Elmedyb .............. | H04R 25/453 381/23.1 |
| 2011/0206226 A1* | 8/2011 | Pandey ................ | H04R 25/453 381/317 |
| 2012/0170766 A1* | 7/2012 | Alves ................... | H04R 1/1083 381/71.11 |
| 2013/0188796 A1* | 7/2013 | Kristensen .......... | H04R 25/453 381/60 |
| 2016/0063988 A1* | 3/2016 | Hendrix ............... | H04R 1/1083 381/71.6 |
| 2016/0066822 A1 | 3/2016 | Shennib et al. | |
| 2019/0045293 A1* | 2/2019 | Blau .................... | A61B 5/0004 |

OTHER PUBLICATIONS

Valente et al., *Intersubject Variability of Real-Ear Sound Pressure Level: Conventional and Insert Earphones*, Washington University School of Medicine, Digital Commons@Becker, 1994, 10 pages.
Sankowsky-Rothe et al., *Reciprocal Measurement of Acoustic Feedback Paths in Hearing Aids*, The Journal of the Acoustical Society of America, 2015, http://doi.org/10.1121/1.4933062, 7 pages.
Yeung et al., *Self-Administered Hearing Loss Screening Using an Interactive, Tablet Play Audiometer with Ear Bud Headphones*, International Journal of Pediatric Otorhinolaryngology 79 (2015), 5 pages.
Fayçal et al., *Computer Audiometer for Hearing Testing*, International Conference on Advances in Electronics and Microelectronics, 978-0-7695-3370-4 © 2008 IEEE, 4 pages.

\* cited by examiner ion to some embodiments.

HEARING DIAGNOSTIC SYSTEM

RELATED APPLICATIONS

The present disclosure claims priority to U.S. provisional application No. 62/840,645 entitled "HEARING DIAGNOSTIC SYSTEM" and filed Apr. 30, 2019, the disclosure of which is incorporated by reference in its entirety.

FIELD OF THE DISCLOSURE

This disclosure relates in general to the field of hearing diagnostics, and more particularly, though not exclusively, to a system and method for self-calibration of audio devices that can be utilized for hearing diagnostics.

BACKGROUND

Legacy hearing testing has involved visiting a special testing facility where hearing could be tested in a controlled environment to ensure accurate results of the testing. Having to visit a special testing facility can be time consuming and can limit a tested population due to the availability of the special testing facilities and the amount of tests that can be performed in a time period by the special testing facility.

BRIEF DESCRIPTION OF THE DRAWINGS

The present disclosure is best understood from the following detailed description when read with the accompanying figures. It is emphasized that, in accordance with the standard practice in the industry, various features are not necessarily drawn to scale, and are used for illustration purposes only. Where a scale is shown, explicitly or implicitly, it provides only one illustrative example. In other embodiments, the dimensions of the various features may be arbitrarily increased or reduced for clarity of discussion.

SUMMARY OF THE DISCLOSURE

Figure 1:
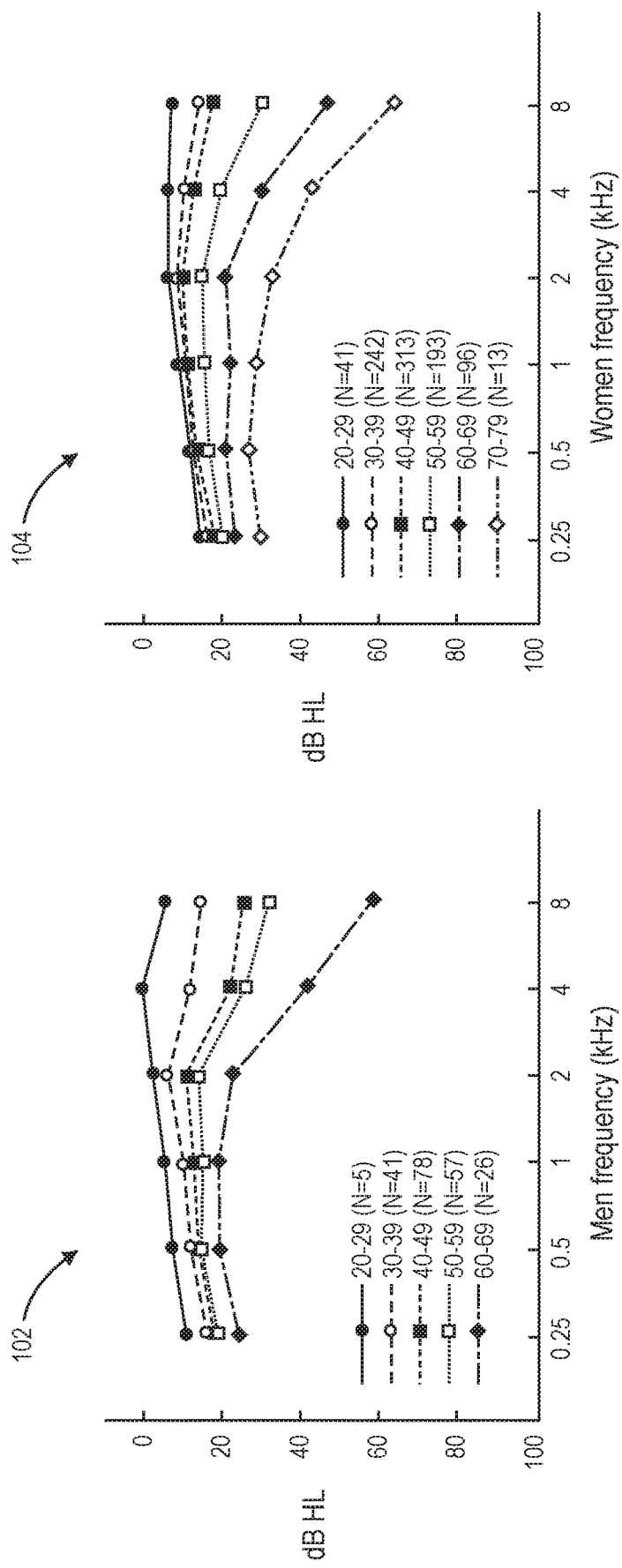
FIG. 1 illustrates hearing profiles of average individuals based on age.

Herein disclosed is a system that may be implemented within headphones to facilitate hearing testing. Implementation of the system in the headphone may include implementation of tone generation circuitry and sound pressure level measurement circuitry being implemented in the headphone limiting the amount of calibration for accurate measurement when performing a hearing test.

DETAILED DESCRIPTION

Hearing and hearing loss are a growing issue in society. The advent of mobile devices and headphones is driving loudness related hearing loss towards younger and younger age groups. The growth in the population experiencing hearing loss creates a desire for more and wider availability of hearing testing to identify hear loss in individuals.

To help facilitate better hearing among a wider populace it is beneficial to be able to easily diagnose hearing. Legacy hearing testing involves visiting a specialist and having a test performed in a controlled environment. This to ensure the accuracy of the measurement results. Having to visit a specialist for hearing testing can be onerous and time consuming.

Self-administered hearing tests using conventional headphones have shown to be feasible within an acceptable error margin as a test vehicle. In particular, assuming that the entire signal chain has been re-calibrated with the conventional headphones, the approach can be feasible.

Conventional headphones used where calibrated, and the test software adjusted, to ensure that the output sound pressure level (SPL) in the self-administered test can match the fully calibrated standard measurement system administered by the specialist in the legacy hearing tests.

Ensuring that the full acoustic signal chain is calibrated is a significant challenge. Further challenges may include the frequency characteristics of the headphones themselves, and the environment in which the measurements are performed. These factors can matter if an accurate measurement is to be performed.

Calibrated Signal Chain

For a closed system it is possible to pre-calibrate the system, such that the SPL of the tones issued into the ear are guaranteed to be a given value. In particular, pre-calibration of a closed system can be utilized to provide for accurate hearing testing without the losses and/or inaccuracies that can occur in non-closed systems.

In a system where the source of test tones is, for example, a smart phone, and the transducer is a mobile headphone, it can be difficult to ensure that when a given SPL is assumed to be played back by the headphone, that said SPL value is actually present. For example, conversions of the test tones between the smart phone and the mobile headphone may cause changes in given SPL value that can cause an actual SPL value of the test tone presented by the mobile headphone being different than the intended SPL of the test tone.

Introducing a feedback signal path from the ear, that allows the system to continuously monitor the SPL of the issued tone, can ensure that a given SPL to be played back by the headphone is actually present. Allowing the system to adjust to gain to the desired SPL level can result in a more correct measurement.

The feedback signal path can include a microphone placed in the ear as part of the transducer. For example, the microphone can be placed within a headphone (such as within a silicone plug of an earbud and/or within the headphone itself), where being placed in the silicone plug can provide little environmental noise. This microphone, if pre-calibrated, can provide a measurement of the SPL in the test subject's ear. Further, circuitry within the headphone can determine an SPL measured by the microphone within the headphone and compensate for a difference between the measured SPL and the SPL intended to be emitting by the headphone. In some embodiments, tone generator circuitry and SPL measurement circuitry may be implemented within the headphone may eliminate inaccuracies that can be caused by transmitting test tones between a smart phone and headphones.

Frequency Characteristic of the Headphones

Normally, part of the signal chain calibration can include the headphones, and hence the frequency characteristic of the headphones and their influence on the measurement result and/or apply linearization filters can be determined. However, as headphones are changed out and/or characteristics of headphones may change due to use, calibration may need to be performed again to maintain accurate hearing measurements.

With no change, the frequency characteristic of the headphone can affect the measurement result. Having a calibrated microphone in the signal path allows for a dynamic adjustment of the output amplitude to compensate for the headphone.

Measurement Environment

The environment in which the user is when the measurement is performed can impact the result. This is why users are placed in a sound proof booth at an audiologist during legacy hearing testing.

For a consumer-based hearing test headset there can be two methods available for controlling the environment. The first is passive attenuation by blocking environmental sounds from the user's ears. The second is to apply Active Noise Cancellation (ANC) to remove the undesired environmental noise from the user's ears.

In some embodiments, ANC is implemented, and the in-ear microphone can be part of a feedback ANC system. In particular, the microphone located within the headphone may detect environmental noise and provide the data related to the detected environmental noise to the system. The system may then apply noise cancellation based on the data related to the detected environmental noise to cancel out the environmental noise.

Microphone Type

It is possible to use any microphone for the system, but it may be beneficial to utilize microelectro-mechanical systems (MEMS) microphones. MEMS microphones may have a nice flow frequency characteristic and good aging effects. For example, the MEMS microphones may have a flat frequency response curve in the range of frequencies that may be utilized for hearing testing.

Utilizing a good microphone (such as a MEMS microphone) can make the rest of the system cheaper to manufacture since the need for per unit calibration can be a lot lower. With a MEMS microphone it is feasible to make a self-calibrating system.

A challenge presented by a MEMS microphone is the maximum SPL it can withstand. Here a multi-element MEMS microphone akin to high SPL MEMS microphone could be beneficial.

When a hearing profile has been attained via measurement it is possible to compare the hearing profile to an average hearing loss profile based on sex and age. Any large deviation from this average profile can be indicative of a hearing condition. Depending on the deviation a preliminary diagnosis can be provided. FIG. 1 illustrates hearing profiles of average individuals based on age. In particular, chart 102 illustrates hearing profiles for males of different ages. Chart 104 illustrates hearing profiles for females of different ages.

One type of hearing loss is conductive hearing loss. Conductive hearing loss results from any condition in the outer or middle ear that interferes with sound passing to the inner ear. Some conditions that can cause conductive hearing loss include excessive wax in the auditory canal, a ruptured eardrum, and work-related conductive hearing loss (such as head injuries, penetration of the eardrum by a sharp object, or any event that ruptures the eardrum or breaks the ossicular chain formed by small bones in the middle ear). Conductive hearing loss can include relatively uniform reduced hearing across all frequencies in hearing tests, with no reduction when sounds are transmitted through bone conduction. Conductive hearing loss may be reversible via medical or surgical treatment.

Figure 2:
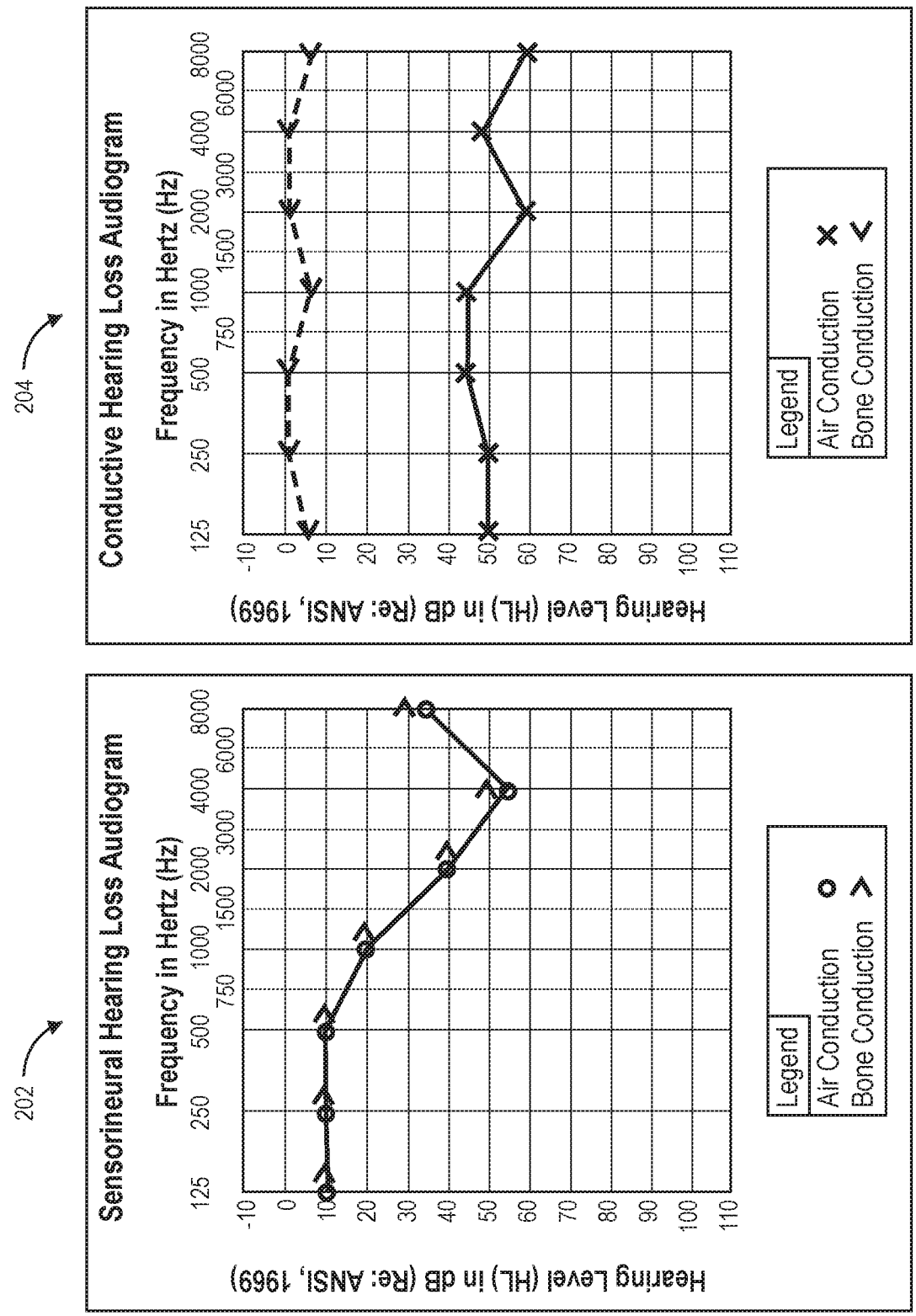
FIG. 2 illustrates example hearing profiles for the types of hearing loss.

Another type of hearing loss is sensorineural hearing loss. Sensorineural hearing loss can be a permanent condition and can be associated with irreversible damage to the inner ear. Sensorineural hearing loss can be caused by the normal aging process and/or excessive noise exposure. FIG. 2 illustrates example hearing profiles for the types of hearing loss. In particular, chart 202 illustrates example hearing profiles for sensorineural hearing loss. Chart 204 illustrates example hearing profiles for conductive hearing loss.

Figure 3:
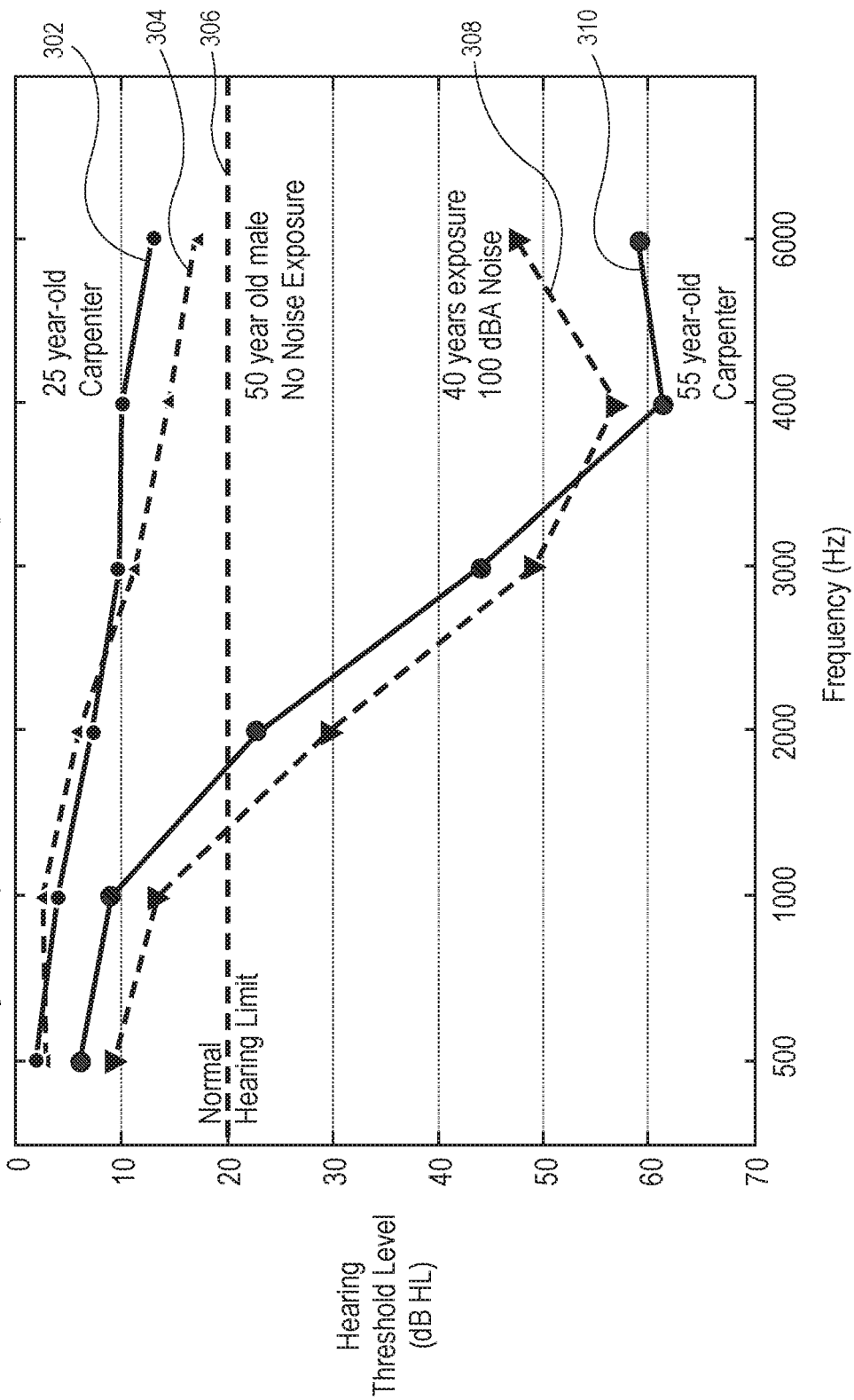
FIG. 3 illustrates hearing loss that may be experienced by a carpenter due to occupational noise exposure.

Sensorineural hearing loss can be caused by occupational noise exposure in some instances. FIG. 3 illustrates hearing loss that may be experienced by carpenters due to occupational noise exposure. Line 302 illustrates a hearing profile of a 25-year old carpenter. Line 304 illustrates a hearing profile of a 50-year old male with noise exposure. Line 306 illustrates a threshold of what is considered a normal hearing limit. Line 308 illustrates a hearing profile of an individual who has experienced 40 years of exposure to 100 A-weighted decibels (dBA) of noise. Line 310 illustrates a hearing profile of 55-year old carpenter.

For hearing profiles, any loss can be a temporary effect, which can also be known as temporary threshold shifts.

Hence a single measurement in isolation may not be enough. In a clinical environment, besides an audiogram measurement, there will also be an interview of recent high noise exposure and a visual inspection of the ear to rule out hearing loss based on visually detectable factors, such as ear wax and disease.

For self-administered hearing tests, it may be beneficial to ensure that not just a single measurement is performed, but also that any large deviation from the norm results in a recommendation to visit a doctor.

Example of Self-Assessment for Medical Diagnostics

A further reason to perform continuous measurements of hearing state can be exemplified by cancer treatments. Cancer treatments can lead to hearing loss, where the reason for hearing loss is partially known [platinum] and partially unknown.

As treatment-based hearing loss may not occur momentarily, having a self-administered hearing test to keep track of any potential changes in hearing for a cancer patient under treatment can be used to adjust to cancer treatment to prevent further damage.

Compensation of Hearing Loss

When an audiogram has been measured by the user via self-assessment it is possible to perform various compensation techniques. For example, the system within the headphone may apply compensation for sounds to be emitted from the headphones based on an audiogram of an individual that may be produced based on hearing testing of the individual. The audiogram utilized for compensation may have been produced from hearing testing performed by the system.

Equalizer

A first technique of performing compensation is to apply an equalization technique. Here the desired audio signal may be attenuated with the inverted audiogram to create a linear frequency characteristic. An additional technique is to add a loudness filter on top based on the measured SPL/volume setting. This may make the sound not only more natural but may also drive a more natural/lower hearing level to potentially prevent further loss of hearing.

Figure 4:
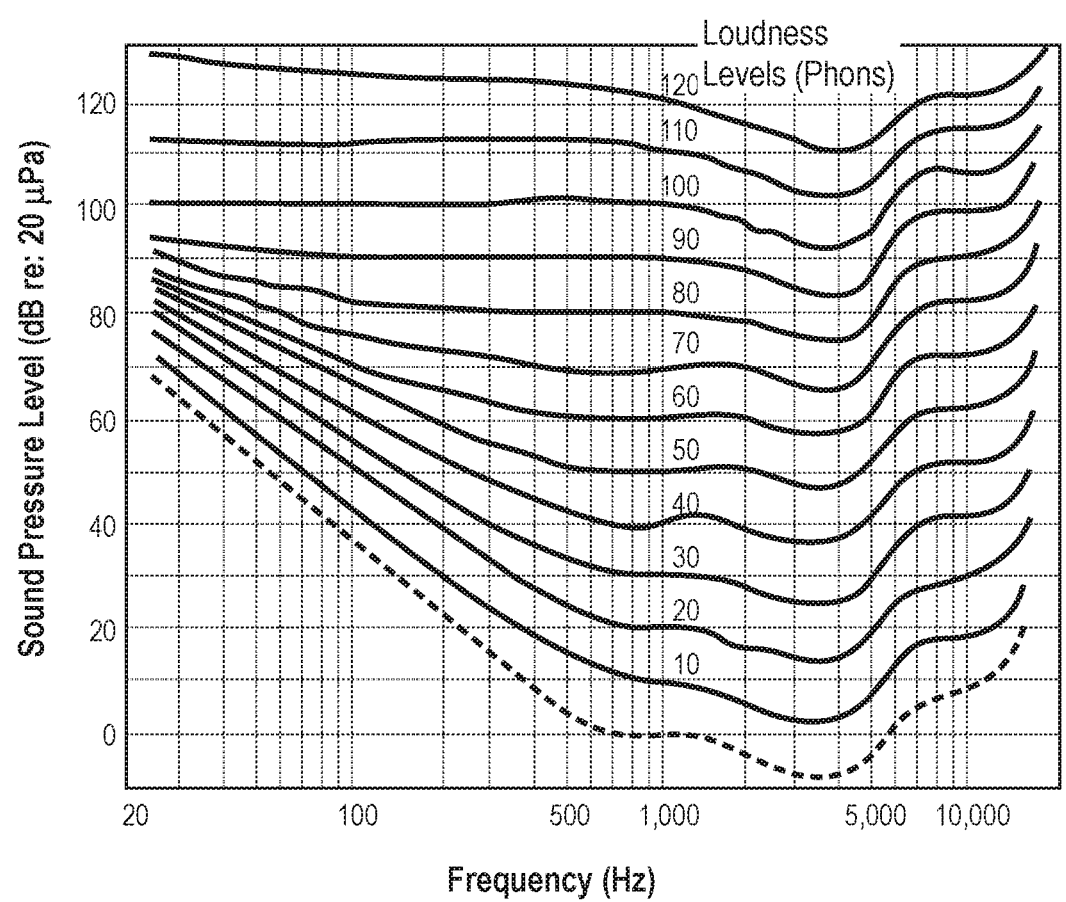
FIG. 4 illustrates a loudness compensation based on Fletcher-Munson Contours.

For dramatic hearing loss compensation, a gradual change may be introduced. This as the brain of the user is already trying to compensate for the loss of hearing. Hence a sudden correction can be disconcerting and even painful for the user. FIG. 4 illustrates a loudness compensation based on Fletcher-Munson Contours. The contours show the SPL at each frequency to produce the same loudness in an average listener. The actual threshold may vary by as much as 10 decibels in either direction.

Compression and Expansion

To help with some aspects of hearing loss, equalization may not be enough. Instead compression of the spectrum can be used. This is a similar thing to the compression seen in frequency modulation (FM)/amplitude modulation (AM) and telephony to adjust for the limited bandwidth of the transmission system.

Compression can be used to conceptually move parts of the sound spectrum that a user cannot hear down into parts of the spectrum that the user can hear in a way that makes it sound natural, to the extent possible.

Expansion can be a method for removing low level sounds from the user of the device. Compensation can involve some level of amplification of the incoming sound. Said amplification also includes low levels of noise/sound, which, if the user is in a quite environment, can become uncomfortable/strange. Expansion can be added to prevent what can be called "super hearing."

Measuring an Audiogram BIAS and BIAS Prevention

For the system a feature is how the audiogram is measured. Assuming the system has been designed as a self-calibrating system with environmental protections included, it can be used to perform self-assessment of hearing.

Standard BIASed Approach

The standard approach for measuring hearing is to subject the user to a sequence of log spaced (for example, mel spaced or cochlear response) sine tones at a moderate sound SPL, followed by a decrease in SPL based on user feedback.

For example, the user is exposed to a 1 kilohertz (kHz) tone at 84 decibels (dB) SPL, if the user acknowledges the tone is heard, the SPL is decreased, and the test repeated until the user cannot hear the tone.

A challenge with the standard approach is that it can introduce an inherent BIAS. Depending on the methodology used, the user's brain can predict the tone issue time and create a phantom tone for the user to hear, even when no tone is actually heard. This BIAS results in a distorted audiogram.

For self-assessment often a direct volume dial and/or volume control is available to the user. This can also lead to a BIAS, as the user knows a tone is playing. This can again cause the brain to create a phantom tone that can distort the audiogram.

For fast testing the number of bands used can be quite low. With a low number of test bands, the resulting audiogram, even though good enough for rudimentary diagnostics, can be too crude for proper compensation.

Unbiased Testing Approaches

To remove bias from the hearing test, predictability can be removed, basically preventing the brain of the user to pattern out the test.

Examples of this is to randomize parts of the test parameters such that the user is not exposed to the same frequency and/or SPL at any given time. For a system like this it is what the user cannot hear can be maintained (such as in memory), such that the user doesn't often hear "nothing". Hearing nothing when a sound is expected can be disconcerting and can cause the user to just press the feedback button.

To minimize search patterns one could use, for example, binary search trees to fill in the audiogram.

Other approaches include using band passed sounds like chirps (which can be referred to as band limited testing). In these approaches, the user can be partially trained in recognizing chirps and what a distorted chirp sounds like. An advantage of using chirps is that it dramatically reduced the audiogram test time.

More advanced tests like speech testing and/or environmental test/experiences can be applied to further remove bias from the testing approach.

Smartphone Based Testing and Compensation

Adding a smartphone into the system can be a seemingly easy way to add a lot of advanced features, like the test generation and compensation. A challenge for smart phones can be the acoustic path from the phone itself to the headset.

The signal path from the phone often includes a wireless/Bluetooth (BT) path in which audio compression can be performed. Audio compression can involve applying a psycho-acoustic filter to the audio being compressed, which distorts the measurements.

The audio from the microphone could potentially be used to fight the distortion of the audio compression, with the caveat that the microphone audio itself can be exposed to audio compression.

Further complexity comes from the fact that most cell phone audio paths themselves may include some sort of equalization to create a specific "sound" that allows a given brand to be easily recognized by the user.

A smart phone system could be constructed so that it does not face the above challenges, but for the legacy smart phones this will not be the case.

Instead the test tones, SPL measurements, and compensation may be created in the headset itself. This can be done, for example, using a specially designed integrated circuit (such as a processor), or a combination of local signal processing and measurement in the headset.

Figure 5:
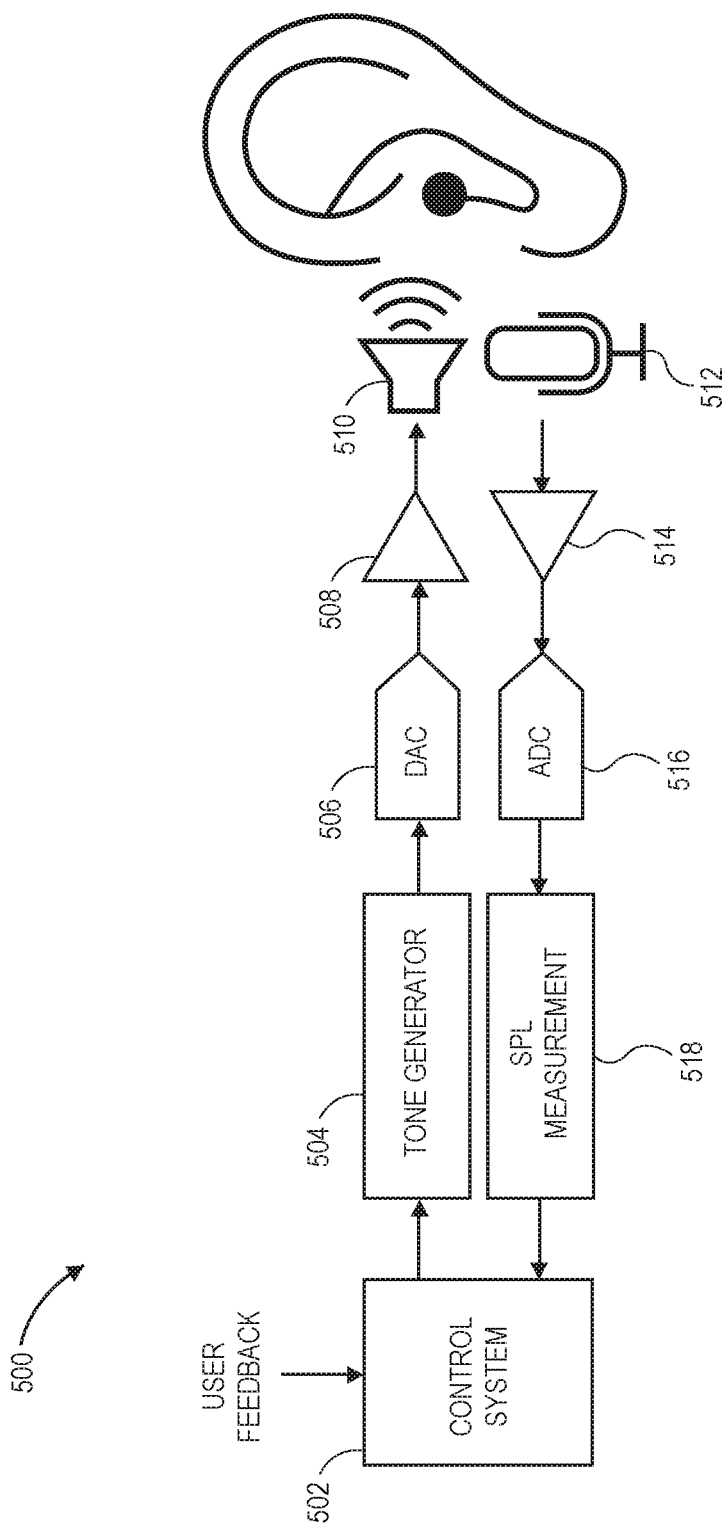
FIG. 5 illustrates an example system that can implement the approaches described throughout this disclosure, according to some embodiments.
Figure 10:
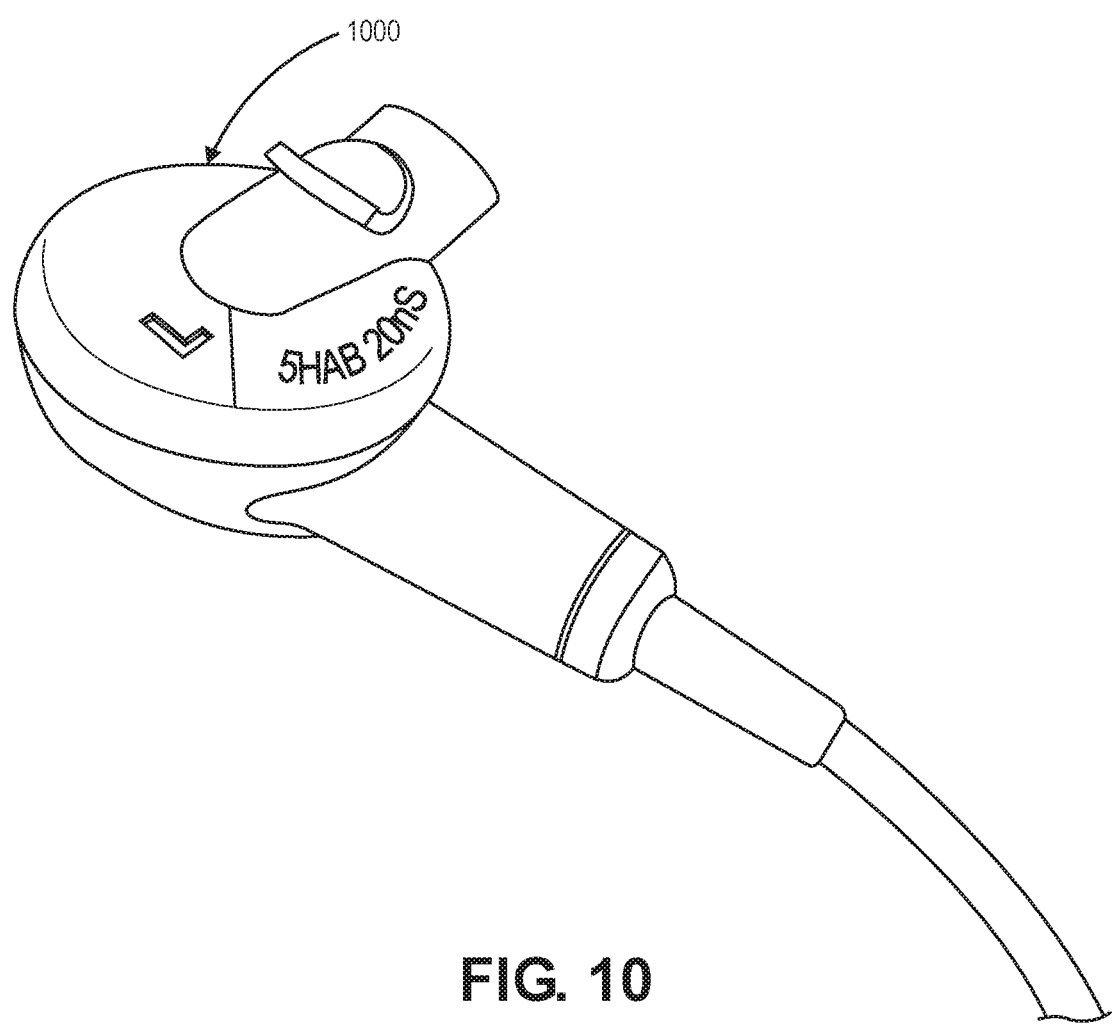
FIG. 10 illustrates an example earbud, according to various embodiments.

FIG. 5 illustrates an example system 500 that can implement the approaches described throughout this disclosure, according to some embodiments. For example, the system 500 may implement the hearing testing approaches, the unbiased testing approaches, and/or the compensation approaches described throughout this disclosure. The system 500 can be implemented in headphones, including an earphone or an earbud of the headphones, such as the earbud 1000 (FIG. 10). In some embodiments, the system 500, or some portion thereof, may be implemented in a processor located within the headphones. In some embodiments, a single earphone or earbud of the headphones may include the system 500, whereas each of the earphones or earbuds of the headphone may include the system 500 in other embodiments.

The system 500 can include a control system 502. The control system 502 can control one or more elements of the system 500. Further, the control system 502 can receive user feedback. The user feedback may indicate that the user heard a tone, the user did not hear a tone, or some combination thereof. The control system 502 may be coupled to a remote device (such as a smart phone) and may communicate with the remote device. The control system 502 may initiate a hearing test in response to a trigger from the remote device, or may initiate a hearing test in response to a user interaction with the headphone, such as the user pressing a button on the headphone.

The system 500 can further include a tone generator 504. The tone generator 504 can generate tones for determining calibration of the system 500. Further, the tone generator 504 can generate tones for hearing testing of the user. The tone generator 504 can generate the tones as digital signals. The tone generator 504 may generate the tones for calibration of the system 500 and/or for the hearing testing of the user in response to signals received from the control system 502.

The tone generator 504 can be coupled to the control system 502 and the control system 502 can cause the tone generator 504 to generate the tones. For example, the control system 502 can output a signal to the tone generator 504 to cause the tone generator 504 to generate a tone that corresponds to the signal. The amplitude and/or frequency of the tone generated by the tone generator 504 may be based on a value of the signal output by the control system 502, an amplitude of the signal output by the control system 502, a frequency of the signal output by the control system 502, a timing offset of the signal output by the control system 502, a voltage offset of the signal output by the control system 502, or some combination thereof. In particular, as the value, amplitude, frequency, timing offset, and/or voltage offset of the signal output by the control system 502 is changed, the tone generator 504 may change the amplitude, frequency, and/or timing offset of the tone. The control system 502 can change the value, amplitude, frequency, timing offset, and/or voltage offset of the signal output by the control system 502 by predefined intervals, according to a predefined algorithm, or randomly change the characteristics.

The system 500 can further include a digital-to-analog converter (DAC) 506. The DAC 506 can be coupled to the tone generator 504 and can receive the digital signals corresponding to the tones from the tone generator 504. The DAC 506 can convert the digital signals received from the tone generator 504 to analog signals. In some embodiments, the tone generator 504 can generate analog signals and the DAC 506 can be omitted.

The system 500 can further include a buffer 508. The buffer 508 may be coupled to the DAC 506 and may receive the analog signals corresponding to the tones from the DAC 506. The buffer 508 may buffer the analog signals and, in some embodiments, can alter an amplitude of the analog signals.

The system 500 can further include a speaker 510. In some embodiments, the speaker 510 may be a speaker of the headphones utilized for producing sounds for a user. The speaker 510 may be coupled to the buffer 508 and may receive the analog signals corresponding to the tones generated by the tone generator 504 from the buffer 508. The speaker 510 may emit sound based on the received analog signals. For example, the speaker 510 may emit the sounds corresponding to the tones generated by the tone generator 504 based on the received analog signals.

SPLs of the sounds emitted by the speaker 510 may be dependent on the amplitude and/or frequency of the tones generated by the tone generator 504. Further, as previously described, the amplitude and/or frequency of the tones are dependent on the signal output by the control system 502. Accordingly, the SPLs of the sounds emitted by the speaker 510 are dependent on the signal output by the control system 502. The control system 502 can be unaware of the SPLs of the sounds to be output by the speaker 510 in response to the signals output by the control system 502. For example, the system 500 may not implement a calibration procedure, which can be required for the control system 502 to be aware of the SPLs of the sounds to be output by the speaker 510 in response to the signals output by the control system 502. In implementing a procedure for hearing testing of a user, the control system 502 may output a signal to the tone generator 504 in accordance with a predefined characteristic scheme or randomly selected without consideration of the SPL of the sound to be output by the speaker 510 corresponding to the signal. The control system 502 may continue to output signals without knowledge of the SPLs of the sounds to be output by the speaker 510 corresponding to the signals.

The system 500 can further include a microphone 512. In some embodiments, the microphone 512 may be a MEMS microphone. The microphone 512 may receive the sound emitted by the speaker 510. For example, the microphone 512 may receive the tones emitted by the speaker 510. The microphone 512 may convert the sounds to an analog, electrical signal.

The system 500 can further include a buffer 514. The buffer 514 may be coupled to the microphone 512 and may receive the analog signals from the microphone 512. The buffer 514 may buffer the analog signals and, in some embodiments, can alter an amplitude of the analog signals.

The system 500 can further include an analog-to-digital converter (ADC) 516. The ADC 516 may receive the analog signals from buffer 514 and convert the analog signals to digital signals.

The system 500 can further include an SPL measurement element 518. The SPL measurement element 518 may be coupled to the ADC 516 and may receive the analog signal from the ADC 516. The SPL measurement element 518 may determine the SPL of the sounds received by the microphone 512 based on the analog signals. For example, the SPL measurement element 518 may determine the SPL of the tones received by the microphone 512 based on the analog signals.

The control system 502 may be coupled to the SPL measurement element 518 and may receive indications of the SPL determined by the SPL measurement element 518 corresponding to each of the tones. Further, the control system 502 may receive user feedback from the user indicating whether the user heard the tone emitted by the speaker. For example, the speaker 510 may emit a tone corresponding to a signal output by the control system 502. The microphone 512 may detect the tone and the SPL measurement element 518 can determine an SPL of the tone. The control system 502 may receive an indication whether the user heard the tone and the SPL of the tone determined by the SPL measurement element 518. The control system 502 may store a data element indicating the determined SPL of the tone and whether the user heard the sound. The control system 502 may continue to output different signals, receive indications of the SPLs of the tones detected by the microphone 512 corresponding to each of the signals output by the control system 502, receive indications whether each of the tones corresponding to the signals were heard by the user, and store data elements for each of the signals indicating the determined SPL of the tone and whether the user heard the tone until the control system 502 determines that the hearing test has been completed. The control system 502 may determine that the hearing test has been completed based on the all signals for a hearing test being output by the control system 502 and/or based on a determination by the control system 502 that an SPL at which the user stops hearing the tones has been determined within a predetermined precision (such as determining that SPL at which user stops hearing the tones can be identified within 5 dBs).

The elements of the system 500 may be co-located within an earphone or an earbud (such as the earbud 1000). For example, the speaker 510 and the microphone 512 may be co-located within the earphone or the earbud. The speaker 510 and the microphone 512 may be directed in the same direction. For example, the speaker 510 and the microphone 512 both may be directed toward an ear of a user of the earphone or earbud when the earphone or earbud is worn by the user. Further, the control system 502, the tone generator 504, the DAC 506, the buffer 508, the buffer 514, the ADC 516, and/or the SPL measurement element 518 may be implemented within one or more integrated circuits (ICs) (such as processors) that are located within the earphone or the earbud.

Figure 6:
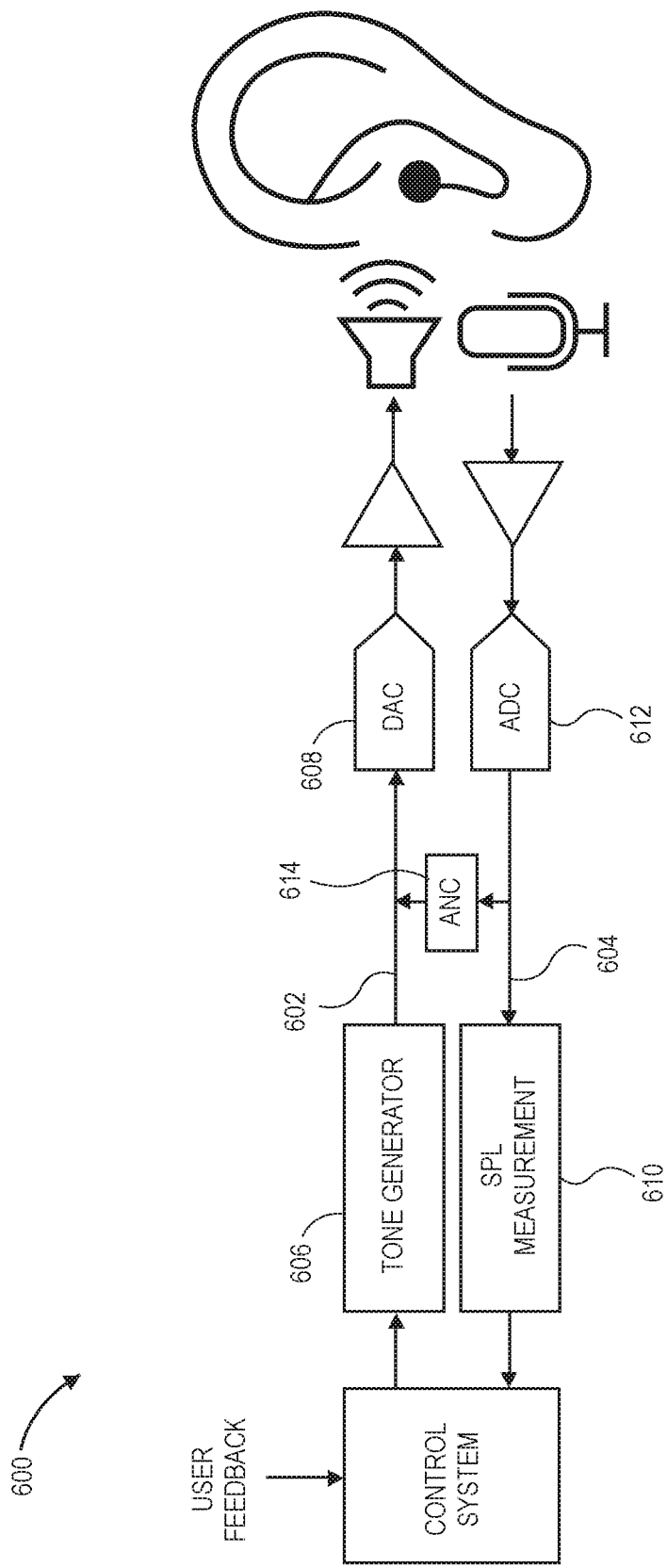
FIG. 6 illustrates an example system that can implement the approaches described throughout this disclosure, according to some embodiments.

FIG. 6 illustrates an example system 600 that can implement the approaches described throughout this disclosure, according to some embodiments. For example, the system 600 may implement the hearing testing approaches, the unbiased testing approaches, and/or the compensation approaches described throughout this disclosure. The system 600 can be implemented in headphones, including an earphone or an earbud of the headphones, such as the earbud 1000 (FIG. 10). In some embodiments, the system 600, or some portion thereof, may be implemented in a processor located within the headphones. In some embodiments, a single earphone or earbud of the headphones may include the system 600, whereas each of the earphones or earbuds of the headphone may include the system 600 in other embodiments. The system 600 can include the same elements of the system 500 (FIG. 5).

The system 600 can include a first coupling element 602 (such as a wire, a trace, or other electrically-conductive elements) that couples a tone generator 606 and a DAC 608, where the tone generator 606 and the DAC 608 have the same features as the tone generator 504 (FIG. 5) and the DAC 506 (FIG. 5), respectively. The system 600 can further include a second coupling element 604 that couples an SPL measurement element 610 and an ADC 612, where the SPL measurement element 610 and the ADC 612 have the same features as the SPL measurement element 518 (FIG. 5) and the ADC 516 (FIG. 5), respectively. The system 600 further includes an ANC element 614. The ANC element 614 is coupled between the first coupling element 602 and the second coupling element 604. The ANC element 614 may detect the signal on the second coupling element 604 and apply noise cancelling to the signal on the first coupling element 602. The ANC element 614 may be co-located within the earphone or the earbud with the other elements. In some embodiments, the IC or ICs that implement other elements of the system 600 can implement the ANC element 614. For example, the IC or ICs may include a control element (such as the control system 502 (FIG. 5)), the tone generator 606, the first coupling element 602, the second coupling element 604, the DAC 608, the ADC 612, the SPL measurement element 610, and/or one or more buffers (such as the buffer 508 (FIG. 5) and the buffer 514 (FIG. 5)).

Figure 7:
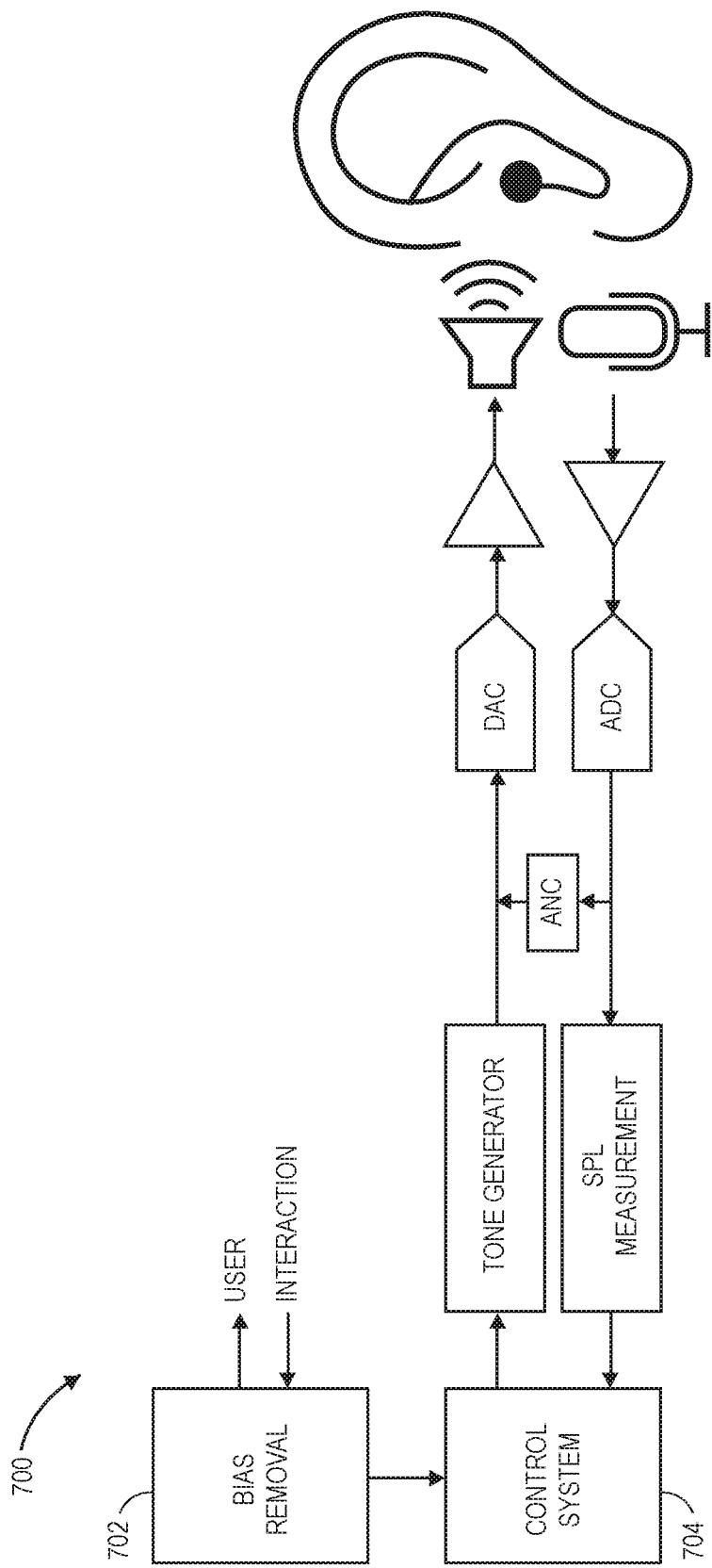
FIG. 7 illustrates an example system that can implement the approaches described throughout this disclosure, according to some embodiments.

FIG. 7 illustrates an example system 700 that can implement the approaches described throughout this disclosure, according to some embodiments. For example, the system 700 may implement the hearing testing approaches, the unbiased testing approaches, and/or the compensation approaches described throughout this disclosure. The system 700 can be implemented in headphones, including an earphone or an earbud of the headphones, such as the earbud 1000 (FIG. 10). In some embodiments, the system 700, or some portion thereof, may be implemented in a processor located within the headphones. In some embodiments, a single earphone or earbud of the headphones may include the system 700, whereas each of the earphones or earbuds of the headphone may include the system 500 in other embodiments. The system 700 can include the same elements of the system 600 (FIG. 6).

The system 700 can further include a BIAS removal element 702. The BIAS removal element 702 can be coupled to a control system 704, where the control system 704 has the same features as the control system 502 (FIG. 5). The BIAS removal element 702 may implement a BIAS removal approach and/or the unbiased testing approach, as described throughout this disclosure. The BIAS removal element 702 may be co-located within the earphone or the earbud with the other elements of the system. In some embodiments, the IC or ICs that implement other elements of the system 700 can implement the BIAS removal element 702.

Figure 8:
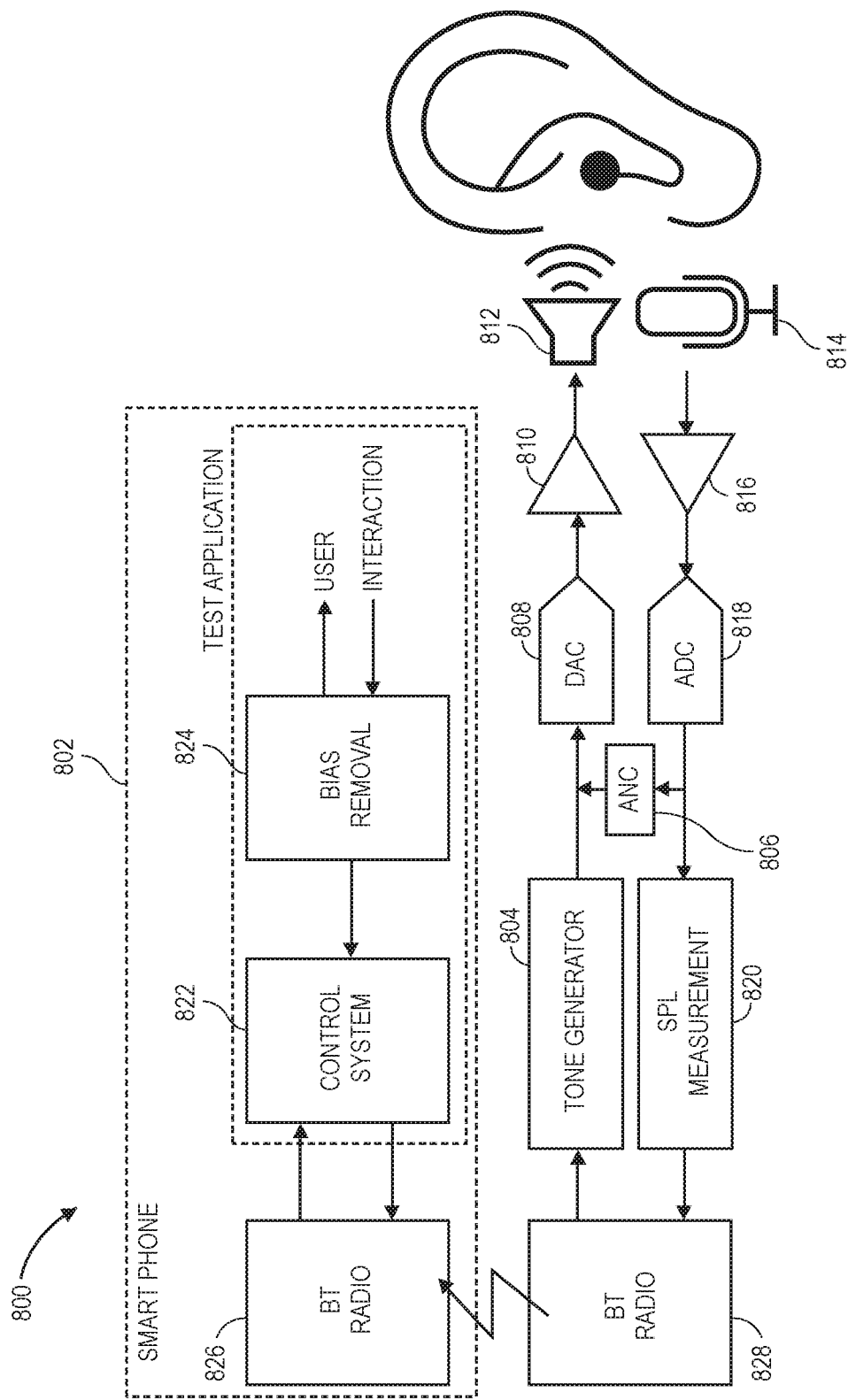
FIG. 8 illustrates an example system that can implement the approaches described throughout this disclosure, according to some embodiments.

FIG. 8 illustrates an example system 800 that can implement the approaches described throughout this disclosure, according to some embodiments. For example, the system 800 may implement the hearing testing approaches, the unbiased testing approaches, and/or the compensation approaches described throughout this disclosure. The system 800, or some portion thereof, can be implemented in headphones, including an earphone or an earbud of the headphones, such as the earbud 1000 (FIG. 10). In some embodiments, the system 800, or some portion thereof, may be implemented in a processor located within the headphones. In some embodiments, a single earphone or earbud of the headphones may include the system 800, whereas each of the earphones or earbuds of the headphone may include the system 800 in other embodiments. The system 800 can include the elements of the system 700 (FIG. 7), although the elements of the system 800 may be separated between the earphone or earbud and a mobile device 802, such as a smart phone. For example, the system 800 can include a tone generator 804, an ANC element 806, a DAC 808, a buffer 810, a speaker 812, a microphone 814, a buffer 816, an ADC 818, and a SPL measurement element 820 co-located within the earphone or earbud. Further, the system 800 can include a control system 822 and a BIAS removal element 824 co-located within the mobile device 802. For example, the control system 822 and the BIAS removal element 824 may be implemented by the mobile device 802.

The mobile device 802 may further include a wireless communication element 826. Further, the system 800 can include a wireless communication element 828 co-located within the earphone or earbud. The wireless communication element 826 and the wireless communication element 828 may implement a wireless communication standard that allows the wireless communication element 826 and the wireless communication element 828 to wirelessly transmit communications between each other. For example, the wireless communication element 826 and the wireless communication element 828 may implement a Bluetooth communication standard in some embodiments. Further, the wireless communication element 826 and the wireless communication element 828 may each comprise a Bluetooth radio in some embodiments. The wireless communication element 826 may be coupled to the control system 822 and may exchange communications with the control system 822.

The wireless communication element 828 may be coupled with the tone generator 804 and the SPL measurement element 820, and may provide communications to the tone generator 804 and receive communications from the SPL measurement element 820. Based on the wireless communication between the wireless communication element 826 and the wireless communication element 828, the control system 822 can communicate with the tone generator 804 and the SPL measurement element 820 via the wireless communication element 826 and the wireless communication element 828.

Figure 9:
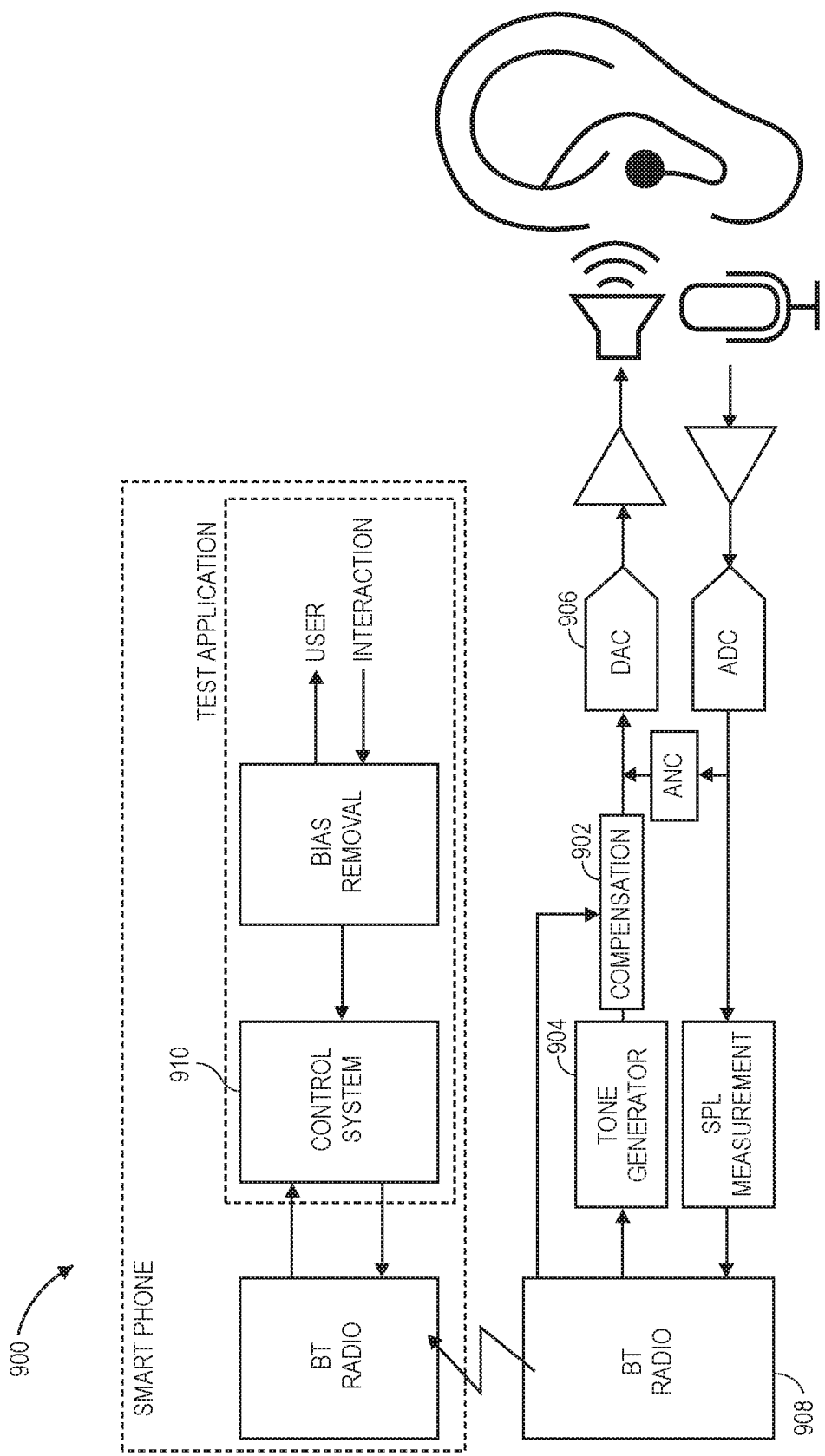
FIG. 9 illustrates an example system that can implement the approaches described throughout this disclosure, according to some embodiments.

FIG. 9 illustrates an example system 900 that can implement the approaches described throughout this disclosure, according to some embodiments. For example, the system 900 may implement the hearing testing approaches, the unbiased testing approaches, and/or the compensation approaches described throughout this disclosure. The system 900 can be implemented in headphones, including an earphone or an earbud of the headphones, such as the earbud 1000 (FIG. 10). In some embodiments, the system 900, or some portion thereof, may be implemented in a processor located within the headphones. In some embodiments, a single earphone or earbud of the headphones may include the system 900, whereas each of the earphones or earbuds of the headphone may include the system 900 in other embodiments. The system 900 can include the same elements as the system 800 (FIG. 8).

The system 900 can further include a compensation element 902. The compensation element 902 may be coupled between a tone generator 904 and a DAC 906, where the tone generator 904 and the DAC 906 have the same features as the tone generator 504 (FIG. 5), and the DAC 506 (FIG. 5), respectively. Further, the compensation element 902 may be coupled to a wireless communication element 908 that can provide for communication between the compensation element 902 and a control system 910, where the wireless communication element 908 and the control system 910 have the features of the wireless communication element 828 (FIG. 8) and the control system 822 (FIG. 8), respectively. The compensation element 902 may receive communications from the control system 910 and utilize the communications to provide compensation to a signal received from the tone generator 904 and provided to the DAC 906 by the compensation element 902. The compensation that may be performed by the compensation element 902 may include performing a reverse equalization on the signal, apply a gain to frequencies within the signal corresponding to hearing loss of the user, lowering frequencies within the signal corresponding to good hearing of the user to match with frequencies corresponding to hearing loss of the user, and/or compression The compensation element 902 may be co-located in the earphone or the earbud with other elements of the system 900 located within the earphone or earbud. In some embodiments, the IC or ICs that implement other elements of the system 700 located within the earphone or earbud can implement the compensation element 902.

FIG. 10 illustrates an example earbud 1000, according to various embodiments. Systems, or portions thereof, described throughout this disclosure can be implemented in the earbud 1000. For example, the system 500 (FIG. 5), the system 600 (FIG. 6), and the system 700 (FIG. 7) may be implemented in the earbud 1000 in some embodiments. Further, portions of the system 800 (FIG. 8) and the system 900 (FIG. 9) may be implemented in the earbud 1000 in some embodiments. A speaker (such as the speaker 510 (FIG. 5) or the speaker 812 (FIG. 8)) and a microphone (such as the microphone 512 (FIG. 5) or the microphone 814 (FIG. 8)) may be located within the earbud 1000 in some embodiments.

Figure 11:
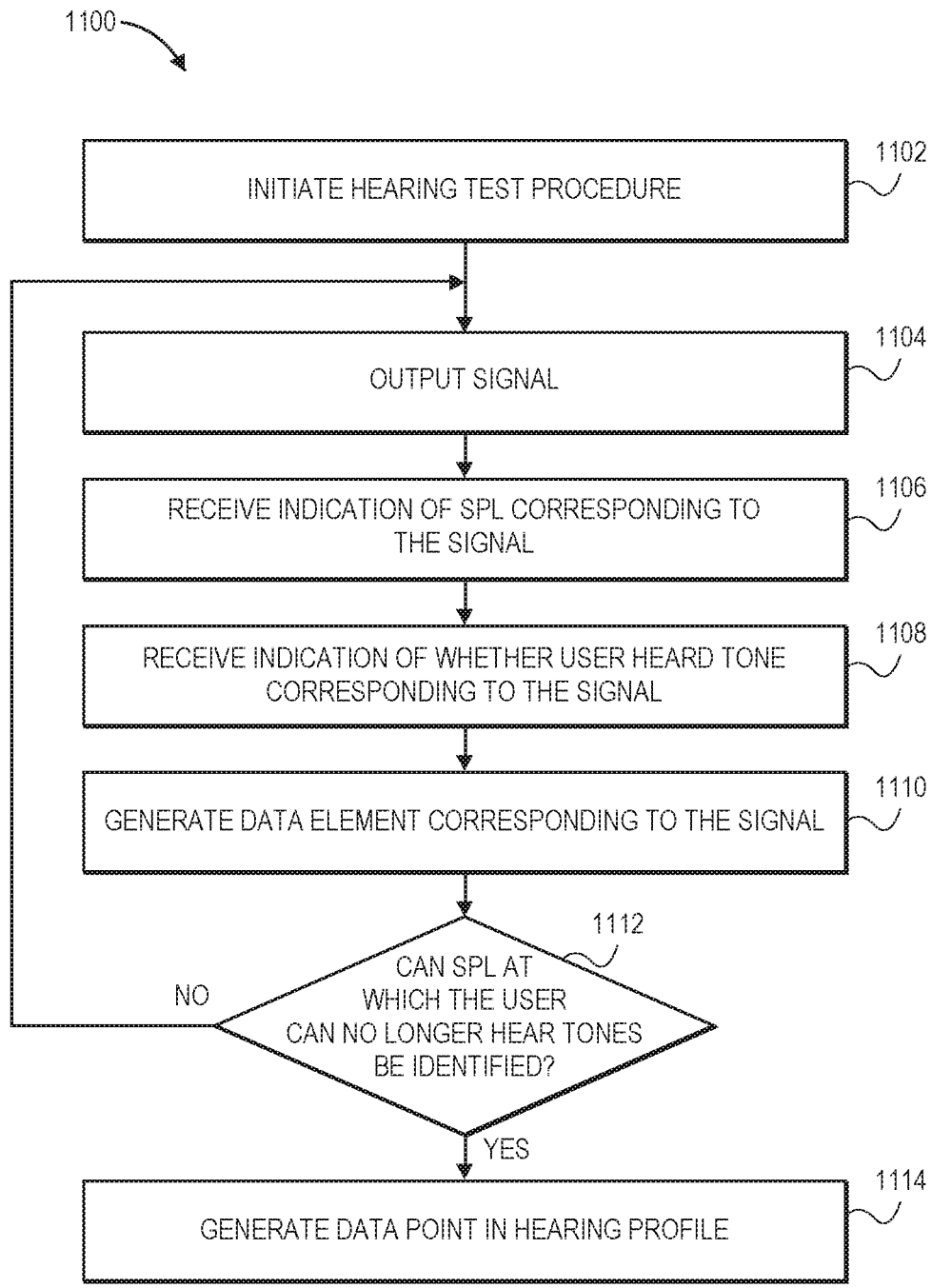
FIG. 11 illustrates an example hearing test procedure, according to various embodiments.

FIG. 11 illustrates an example hearing test procedure 1100, according to various embodiments. The hearing test procedure 1100 may be implemented by a control system of any of the control systems disclosed herein, such as the control system 502 (FIG. 5), the control system 704 (FIG. 7), the control system 822 (FIG. 8), and the control system 910 (FIG. 9).

In stage 1102, the hearing test procedure may be initiated.

In stage 1104, the control system may output a signal. The signal output by the control system may display characteristics of a signal that has not been output during the current hearing test procedure 1100. For example, the signal may have a different value, amplitude, frequency, timing offset, and/or voltage offset than signals previously output by the control system. The control system may determine the characteristics of the signal based on a predefined characteristic scheme or may be randomly determined, and the control system may generate the signal with the characteristics. In some embodiments, the predefined characteristic scheme may include increasing or decreasing one or more characteristics of the signal from the immediately preceding signal by a predefined amount. In some embodiments, the predefined characteristic scheme may include increasing or decreasing one or more of the characteristics of the signal based on whether the user indicated hearing the tone corresponding to the immediately preceding signal, where the amount of the change or changes can be determined based on one or more of the previous preceding signals.

In stage 1106, the control system may receive an indication of an SPL corresponding to the signal. The control system may receive the SPL from an SPL measurement element, such as the SPL measurement element 518 (FIG. 5), the SPL measurement element 610 (FIG. 6), and the SPL measurement element 820 (FIG. 8).

In stage 1108, the control system may receive an indication of whether the user heard a tone corresponding to the signal. The control system may receive user feed indicating whether the user heard the tone corresponding to the signal.

In stage 1110, the control system may generate and store a data element corresponding to the signal. The data element may include an indication of the SPL corresponding to the signal and an indication of whether the user heard the tone corresponding to the signal.

In stage 1112, the control system can determine whether an SPL at which the user can no longer hear the tones can be identified. For example, the control system can determine whether a group of signals to be outputted for the hearing test procedure had been outputted by the control system and analyze the data elements corresponding to the signals to determine an SPL at which the user can no longer hear the tones. In other embodiments, the control system can analyze the data elements corresponding to the signals output by the control system in the current hearing test procedure and determine whether the SPL at which the user can no longer hear the tones can be determined within a predefined precision. The control system can determine the SPL at which the user can no longer hear the tones based on the indications of the SPLs and the corresponding indications of whether the user can hear the tones in the data elements. If the SPL at which the user can no longer hear the tones cannot be determined, the procedure 1100 can proceed to stage 1104. If the SPL at which the user can no longer hear the tones can be determined, the procedure 1100 can proceed to stage 1114.

In stage 1114, the control system may generate a data point in a hearing profile for the user based on the SPL at which the user can no longer hear the tones.

The foregoing outlines features of one or more embodiments of the subject matter disclosed herein. These embodiments are provided to enable a person having ordinary skill in the art (PHOSITA) to better understand various aspects of the present disclosure. Certain well-understood terms, as well as underlying technologies and/or standards may be referenced without being described in detail. It is anticipated that the PHOSITA will possess or have access to background knowledge or information in those technologies and standards sufficient to practice the teachings of the present disclosure.

The PHOSITA will appreciate that they may readily use the present disclosure as a basis for designing or modifying other processes, structures, or variations for carrying out the same purposes and/or achieving the same advantages of the embodiments introduced herein. The PHOSITA will also recognize that such equivalent constructions do not depart from the spirit and scope of the present disclosure, and that they may make various changes, substitutions, and alterations herein without departing from the spirit and scope of the present disclosure.

Note that the activities discussed above with reference to the FIGURES are applicable to any integrated circuit that involves signal processing (for example, gesture signal processing, video signal processing, audio signal processing, analog-to-digital conversion, digital-to-analog conversion), particularly those that can execute specialized software programs or algorithms, some of which may be associated with processing digitized real-time data. Certain embodiments can relate to multi-DSP, multi-ASIC, or multi-SoC signal processing, floating point processing, signal/control processing, fixed-function processing, microcontroller applications, etc. In certain contexts, the features discussed herein can be applicable to medical systems, scientific instrumentation, wireless and wired communications, radar, industrial process control, audio and video equipment, current sensing, instrumentation (which can be highly precise), and other digital-processing-based systems. Moreover, certain embodiments discussed above can be provisioned in digital signal processing technologies for medical imaging, patient monitoring, medical instrumentation, and home healthcare. This could include, for example, pulmonary monitors, accelerometers, heart rate monitors, or pacemakers, along with peripherals therefor. Other applications can involve automotive technologies for safety systems (e.g., stability control systems, driver assistance systems, braking systems, infotainment and interior applications of any kind). Furthermore, powertrain systems (for example, in hybrid and electric vehicles) can use high-precision data conversion, rendering, and display products in battery monitoring, control systems, reporting controls, maintenance activities, and others. In yet other example scenarios, the teachings of the present disclosure can be applicable in the industrial markets that include process control systems that help drive productivity, energy efficiency, and reliability. In consumer applications, the teachings of the signal processing circuits discussed above can be used for image processing, auto focus, and image stabilization (e.g., for digital still cameras, camcorders, etc.). Other consumer applications can include audio and video processors for home theater systems, DVD recorders, and high-definition televisions. Yet other consumer applications can involve advanced touch screen controllers (e.g., for any type of portable media device). Hence, such technologies could readily part of smartphones, tablets, security systems, PCs, gaming technologies, virtual reality, simulation training, etc.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

The particular embodiments of the present disclosure may readily include a system on chip (SoC) central processing unit (CPU) package. An SoC represents an integrated circuit (IC) that integrates components of a computer or other electronic system into a single chip. It may contain digital, analog, mixed-signal, and radio frequency functions: all of which may be provided on a single chip substrate. Other embodiments may include a multi-chip-module (MCM), with a plurality of chips located within a single electronic package and configured to interact closely with each other through the electronic package. Any module, function, or block element of an ASIC or SoC can be provided, where appropriate, in a reusable "black box" intellectual property (IP) block, which can be distributed separately without disclosing the logical details of the IP block. In various other embodiments, the digital signal processing functionalities may be implemented in one or more silicon cores in application-specific integrated circuits (ASICs), field-programmable gate arrays (FPGAs), and other semiconductor chips.

In some cases, the teachings of the present disclosure may be encoded into one or more tangible, non-transitory computer-readable mediums having stored thereon executable instructions that, when executed, instruct a programmable device (such as a processor or DSP) to perform the methods or functions disclosed herein. In cases where the teachings herein are embodied at least partly in a hardware device (such as an ASIC, IP block, or SoC), a non-transitory medium could include a hardware device hardware-programmed with logic to perform the methods or functions disclosed herein. The teachings could also be practiced in the form of Register Transfer Level (RTL) or other hardware description language such as VHDL or Verilog, which can be used to program a fabrication process to produce the hardware elements disclosed.

In example implementations, at least some portions of the processing activities outlined herein may also be implemented in software. In some embodiments, one or more of these features may be implemented in hardware provided external to the elements of the disclosed figures, or consolidated in any appropriate manner to achieve the intended functionality. The various components may include software (or reciprocating software) that can coordinate in order to achieve the operations as outlined herein. In still other embodiments, these elements may include any suitable algorithms, hardware, software, components, modules, interfaces, or objects that facilitate the operations thereof.

Additionally, some of the components associated with described microprocessors may be removed, or otherwise consolidated. In a general sense, the arrangements depicted in the figures may be more logical in their representations, whereas a physical architecture may include various permutations, combinations, and/or hybrids of these elements. It is imperative to note that countless possible design configurations can be used to achieve the operational objectives outlined herein. Accordingly, the associated infrastructure has a myriad of substitute arrangements, design choices, device possibilities, hardware configurations, software implementations, equipment options, etc.

Any suitably-configured processor component can execute any type of instructions associated with the data to achieve the operations detailed herein. Any processor disclosed herein could transform an element or an article (for example, data) from one state or thing to another state or thing. In another example, some activities outlined herein may be implemented with fixed logic or programmable logic (for example, software and/or computer instructions executed by a processor) and the elements identified herein could be some type of a programmable processor, programmable digital logic (for example, an FPGA, an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof. In operation, processors may store information in any suitable type of non-transitory storage medium (for example, random access memory (RAM), read only memory (ROM), FPGA, EPROM, electrically erasable programmable ROM (EEPROM), etc.), software, hardware, or in any other suitable component, device, element, or object where appropriate and based on particular needs. Further, the information being tracked, sent, received, or stored in a processor could be provided in any database, register, table, cache, queue, control list, or storage structure, based on particular needs and implementations, all of which could be referenced in any suitable timeframe. Any of the memory items discussed herein should be construed as being encompassed within the broad term 'memory.' Similarly, any of the potential processing elements, modules, and machines described herein should be construed as being encompassed within the broad term 'microprocessor' or 'processor.' Furthermore, in various embodiments, the processors, memories, network cards, buses, storage devices, related peripherals, and other hardware elements described herein may be realized by a processor, memory, and other related devices configured by software or firmware to emulate or virtualize the functions of those hardware elements.

Computer program logic implementing all or part of the functionality described herein is embodied in various forms, including, but in no way limited to, a source code form, a computer executable form, a hardware description form, and various intermediate forms (for example, mask works, or forms generated by an assembler, compiler, linker, or locator). In an example, source code includes a series of computer program instructions implemented in various programming languages, such as an object code, an assembly language, or a high-level language such as OpenCL, RTL, Verilog, VHDL, Fortran, C, C++, JAVA, or HTML for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

In the discussions of the embodiments above, the capacitors, buffers, graphics elements, interconnect boards, clocks, DDRs, camera sensors, converters, inductors, resistors, amplifiers, switches, digital core, transistors, and/or other components can readily be replaced, substituted, or otherwise modified in order to accommodate particular circuitry needs. Moreover, it should be noted that the use of complementary electronic devices, hardware, non-transitory software, etc. offer an equally viable option for implementing the teachings of the present disclosure.

In one example embodiment, any number of electrical circuits of the FIGURES may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself. In another example embodiment, the electrical circuits of the FIGURES may be implemented as standalone modules (e.g., a device with associated components and circuitry configured to perform a specific application or function) or implemented as plug-in modules into application-specific hardware of electronic devices.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this disclosure. In certain cases, it may be easier to describe one or more of the functionalities of a given set of flows by only referencing a limited number of electrical elements. It should be appreciated that the electrical circuits of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Example Implementations

The following examples are provided by way of illustration.

Example 1 may include a system to be located within headphones for performing hearing testing, comprising a tone generator to receive an indication of a tone to be emitted from the headphones, and cause the tone to be emitted by a speaker within the headphones, and a sound pressure level (SPL) measurement element to receive an indication of the tone detected by a microphone within the headphones; and determine an SPL of the tone detected by the microphone, wherein the SPL is to be used to verify that the SPL is equal to an intended SPL for the tone.

Example 2 may include the system of example 1, wherein SPL is to be used to calibrate the tone generator for subsequent tones to be emitted by the speaker.

Example 3 may include the system of example 1, further comprising an active noise cancellation (ANC) element coupled to an output of the tone generator and an input of the SPL measurement element, the ANC element to determine an indication of sounds detected by the microphone, the sounds being separate from the tone, and apply ANC with the speaker based on the indication of the sounds to noise cancel the sounds.

Example 4 may include the system of example 1, further comprising a compensation element coupled to an output of the tone generator, the compensation element to apply compensation to signal provided to the compensation element.

Example 5 may include the system of example 1, further comprising a control system to provide the indication of the tone to be emitted to the tone generator, and utilize the SPL of the tone to calibrate the tone generator for subsequent tones to be emitted by the speaker.

Example 6 may include the system of example 5, wherein the control system is further to generate an audiogram based on the hearing testing, and cause compensation to be applied to sounds to be emitted from the speaker.

Example 7 may include the system of example 5, wherein the control system is further to detect an indication that a hearing test is to be performed, and wherein the control system is to provide the indication of the tone in response to detection of the indication that the hearing test is to be performed.

Example 8 may include the system of example 1, further comprising a bias removal element to cause an unbiased approach to be utilized for the hearing testing.

Example 9 may include the system of example 1, wherein the system is implemented within a processor located within the headphones.

Example 10 may include headphones, comprising a speaker to emit tones, a tone generator coupled to the speaker to cause the speaker to emit a first tone, a microphone to detect the first tone emitted by the speaker, and a sound pressure level (SPL) measurement element coupled to the microphone to determine an SPL of the first tone emitted by the speaker based on detection of the first tone by the microphone, wherein the determined SPL is to be utilized to determine whether to adjust SPLs of the tones to be emitted by the speaker.

Example 11 may include the headphones of example 10, further comprising a control system coupled to the tone generator and the SPL measurement element, the control system to compare the determined SPL of the first tone with an intended SPL for the first tone, and control the SPLs of the tones based on a results of the comparison of the determined SPL with the intended SPL.

Example 12 may include the headphones of example 11, wherein the speaker is further to emit sounds provided by a remote device, wherein the control system is further to control SPLs of the sounds based on the results of the comparison of the determined SPL with the intended SPL.

Example 13 may include the headphones of example 11, wherein the control system is further to detect an indication that a hearing test is to be performed, and provide an indication to the tone generator to cause the speaker to emit the first tone in response to detection of the indication that the hearing test is to be performed.

Example 14 may include the headphones of example 11, further comprising a bias removal element coupled to an input of the control system, wherein the bias removal element is to implement an unbiased testing approach for hearing testing to be performed by the headphones.

Example 15 may include the headphones of example 10, further comprising an active noise cancellation (ANC) element coupled to the speaker and the microphone, the ANC element to identify environmental noises detected by the microphone, and apply ANC to the tones to be emitted by the speaker, the ANC based on the identified environmental noises.

Example 16 may include the headphones of example 15, further comprising a digital-to-analog converter (DAC) coupled between the tone generator and the speaker, wherein the ANC element is coupled to the speaker between the tone generator and the DAC, and an analog-to-digital converter (ADC) coupled between the SPL measurement element and microphone, wherein the ANC element is coupled to the microphone between the SPL measurement element and the ADC.

Example 17 may include the headphones of example 10, wherein the speaker, the tone generator, the microphone, and the SPL measurement element co-located within an earphone or an earbud of the microphone.

Example 18 may include a method of performing a hearing test by headphones, comprising causing, by a tone generator located within the headphones, a tone to be emitted by a speaker of the headphones, detecting, by a microphone located within the headphones, the tone emitted by the speaker, determining, by a sound pressure level (SPL) located within the headphones, an SPL of the tone emitted by the speaker, comparing the determined SPL of the tone with an intended SPL for the tone, and determining whether to adjust SPLs of subsequent tones to be emitted by the speaker based on the comparison of the determined SPL of the tone with the intended SPL of the tone.

Example 19 may include the method of example 18, further comprising identifying, by an active noise cancellation (ANC) element within the headphones, environmental noise detected by the microphone, and applying, by the ANC element, ANC to the subsequent tones to be emitted by the speaker.

Example 20 may include the method of example 18, further comprising applying, by a compensation element within the headphones, compensation to sounds to be emitted by the speaker, the compensation based on the comparison of the determined SPL of the tone with the intended SPL of the tone.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke 35 U.S.C. § 112(f) as it exists on the date of the filing hereof unless the words "means for" or "steps for" are specifically used in the particular claims; and (b) does not intend, by any statement in the disclosure, to limit this disclosure in any way that is not otherwise reflected in the appended claims.

What is claimed is:

1. A system comprising:
a tone generator to:
receive an indication of a tone to be emitted from headphones, and
output a first signal to cause a speaker to emit the tone;
a digital-to-analog converter (DAC) to generate an analog signal indicative of the tone by converting a signal indicative of the first signal from a digital domain to an analog domain;
a speaker to emit the tone based on. the analog signal;
a microphone to detect the tone emitted by the speaker;
an analog-to-digital converter (ADC) to generate a digital signal. indicative of the tone detected by the microphone by converting a second signal indicative of the tone detected by the microphone from the analog domain to the digital domain;
a sound pressure level (SPL) measurement element to:
receive an indication of the tone detected by the microphone, and
determine are SPL of the tone detected by the microphone, wherein the SPL is to be used to verify that the SPL is equal to an intended SPL for the tone, the SPL measurement element being separate from and coupled to the microphone via at least the ADC; and
a compensation element coupled to an output of the tone generator, the compensation element to apply compensation to the first signal,
wherein each of the tone generator, the DAC, the speaker, the microphone, the ADC, and the SPL measurement element is integrated into the headphones.

2. The system of claim 1, wherein the SPL of the tone is to he used to calibrate the tone generator for subsequent tones to be emitted by the speaker.

3. The system of claim 1, further comprising an active noise cancellation (ANC) element coupled to an output of the tone generator and an input of the SPL measurement element, the ANC element to:
determine an indication of sounds detected by the microphone, the sounds being separate from the tone; and
apply ANC with the speaker based on the indication of the sounds to noise cancel the sounds.

4. The system of claim 1, further comprising a control system to:
provide the indication of the tone to be emitted to the tone generator; and
utilize the SPL of the tone to calibrate the tone generator for subsequent tones to be emitted by the speaker.

5. The system of claim 4, wherein the control system is further to:
generate an audiogram based on hearing testing; and
cause the compensation element to apply compensation to sounds to be emitted from the speaker based on the audiogram, wherein the compensation comprises reverse equalization.

6. The system of claim 4, wherein the control system is further to detect an indication that a hearing test is to be performed, and wherein the control system is to provide the indication of the tone in response to detection of the indication that the hearing test is to be performed.

7. The system of claim 1, further comprising a bias removal element to cause an unbiased approach to be utilized for hearing testing.

8. The system of claim 1, wherein the compensation element comprises a loudness filter based on the SPL of the tone and a volume setting.

9. The system of claim 1, wherein the compensation element is to:
apply a gain to a first set of frequencies within the first signal, the first set of frequencies corresponding to hearing loss of a user, and not apply a gain to a second set of frequencies within the first signal.

10. The system of claim 1, wherein the compensation element is to introduce a gradual change to signals output by the tone generator and provided to the compensation element.

11. Headphones, comprising:
a speaker to emit tones;
a tone generator to output a first signal to cause the speaker to emit a first tone:
a digital-to-analog converter (DAC) coupled between the tone generator and the speaker;
a microphone to detect the first tone;
a sound pressure level (SPL) measurement element coupled to the microphone to determine an SPL of the first tone speaker based on detection of the first tone by the microphone, wherein the SPL of the first tone is to be utilized to determine whether to adjust SPLs of the tones emitted by the speaker;
an analog-to-digital converter (ADC) coupled between the SRL measurement element and the microphone; and
a compensation element coupled to an output of the tone generator, the compensation element to apply compensation to the first signal.

12. The headphones of claim 11, further comprising a control system coupled to the tone generator and the SPL measurement element, the control system to:
compare the SPE of the first tone with an intended SPL for the first tone; and
control the SPLs of the tones based on results of the comparison of the SPL of the first tone with the intended SPL.

13. The headphones of claim 12, wherein the speaker is further to emit sounds provided by a remote device, wherein the control system is further to control SPLs of the sounds based on the results of the comparison of the SPL of the first tone with the intended SPL.

14. The lheadphones of claim 12, wherein the control system is further to:
detect an indication that a hearing test is to be performed; and
provide a second indication to the tone generator to cause the speaker to emit the lrst tone in response to detection of the indication that the hearing test is to be performed.

15. The headphones of claim 12, further comprising a bias removal element coupled to an input of the control system, wherein the bias removal element is to implement an unbiased testing approach for hearing testing to be performed by the headphones.

16. The headphones of claim 11, further comprising an active noise cancellation (ANC) element coupled to the speaker and the microphone, the ANC element to:
identify environmental noises detected. by the microphone; and
apply ANC to the tones emitted by the speaker, the ANC based on the identified environmental noises.

17. The headphones of claim 16, wherein:
the ANC element is coupled to the speaker between the tone generator and the DAC; and
the ANC element is coupled to the microphone between the SPL measurement element and the ADC.

18. The headphones of claim 11, wherein the speaker, the tone generator, the microphone, and the SPL measurement element co-located within an earphone or an earbud of the headphones.

19. A method comprising:
    causing, by a tone generator located within headphones, a tone to be emitted by a speaker of the headphones;
    detecting, by a microphone located within the headphones, the tone;
    determining, by a sound pressure level (SPL) measurement element integrated into the headphones and coupled to the microphone, an SPL of the tone;
    comparing the of the tone with an intended SPL for the tone, yielding a comparison result;
    determining whether to adjust SPLs of subsequent tones to-be emitted by the speaker based on the comparison result; and
    applying, by a compensation element within the headphones, compensation to sounds emitted by the speaker, the compensation based on the comparison of the SPL of the tone with the intended SPL for the tone,
    wherein applying the compensation includes performing a reverse equalization, applying a gain to frequencies corresponding to hearing loss of a user, lowering frequencies other than the frequencies corresponding to the hearing loss of the user, and compression.

20. The method of claim 19, further comprising:
    identifying, by an active noise cancellation (ANC) element within the headphones, environmental noise detected by the microphone; and
    applying, by the ANC element, ANC to the subsequent tones emitted by the speaker.

* * * * *